United States Patent [19]

Jackson

[11] Patent Number: 4,872,870
[45] Date of Patent: Oct. 10, 1989

[54] FUSED LAMINATED FABRIC AND PANTY LINER INCLUDING SAME

[75] Inventor: Lauren Jackson, Yardley, Pa.

[73] Assignee: Chicopee, New Brunswick, N.J.

[21] Appl. No.: 262,111

[22] Filed: Oct. 19, 1988

Related U.S. Application Data

[60] Continuation of Ser. No. 72,837, Jul. 13, 1987, abandoned, which is a division of Ser. No. 641,159, Aug. 16, 1984, Pat. No. 4,737,404.

[51] Int. Cl.$^4$ ............................................. A61F 13/00
[52] U.S. Cl. .................................... 604/366; 604/380
[58] Field of Search ................ 604/365, 366, 380, 378

[56] References Cited

U.S. PATENT DOCUMENTS

| | | | |
|---|---|---|---|
| 3,855,046 | 12/1974 | Hansen et al. | 604/366 |
| 3,921,639 | 11/1975 | Cepuritis | 604/378 |
| 4,081,582 | 3/1978 | Butterworth et al. | 428/284 |
| 4,100,324 | 7/1978 | Anderson et al. | 604/366 |
| 4,160,059 | 7/1979 | Samejima | 428/298 |
| 4,480,000 | 10/1984 | Watanabe et al. | 604/366 |
| 4,536,440 | 8/1985 | Berg | 428/299 |
| 4,542,060 | 9/1985 | Yoshida et al. | 428/284 |
| 4,654,038 | 3/1987 | Sakurai | 604/378 |

Primary Examiner—C. Fred Rosenbaum
Assistant Examiner—Denise Whelton

[57] ABSTRACT

A laminate and method of making the same, comprising a first fibrous layer thermobonded to fusible thermoplastic fibers entangled into the surface of a second fibrous layer, and a panty liner incorporating such a laminate at the garment facing side thereof.

11 Claims, 4 Drawing Sheets

FUSED LAMINATED FABRIC AND PANTY LINER INCLUDING SAME

This is a continuation of application Ser. No. 72,837, filed Jul. 13, 1987 now abandoned. This is a division, of application Ser. No. 641,159, filed Aug. 16, 1984 now U.S. Pat. No. 4,737,404.

BACKGROUND OF THE INVENTION

Entangled nonwoven fabrics have been well known for many years, and have been used in a variety of products such as aprons, towels, wipes, and facing layers for disposable absorbent articles, such as sanitary napkins and diapers. Such fabrics are typically formed by subjection of a loose array of fibers on a foraminous screen to high pressure liquid jets to displace and entangle fibers in relatively densely entangled areas which are interconnected by less dense fiber bands or bundles. A method and apparatus for forming such an entangled nonwoven fabric is disclosed in detail in Evans U.S Pat. No. 3,485,706. Such fabrics rely for strength on interfiber frictional engagement, and when increased fabric strength is required, an additive adhesive has been used.

The prior art is also replete with examples of fabrics formed of thermoplastic fibers, such as polyethylene and polypropylene, which are heat fused to another.

Prior to the present invention it has also been known to secure plural fabric layers, including layers formed of thermoplastic and non-thermoplastic fibers, to one another to form a laminated structure and adhesive binders have typically been used to join the layers together. Fibrous layers have also been heat laminated with a thermoplastic scrim. In addition, unentangled fibrous layers containing thermoplastic binder material or binder fibers at least at one surface thereof, have been heat laminated to films or other fabric layers. However, due to the lack of entangling, these fabrics do not achieve the fabric strength and resistance to delamination of the laminates of the present invention.

It has also been known in the past to form fabrics of conjugate or bicomponent fibers. Such fibers are typically constructed of an outer component having a melting point lower than the melting point of the inner component thereof, so that upon heating the outer component will melt and upon subsequent cooling will solidify and act as a binder to give the resulting fabric strength and integrity. Fabrics formed of bicomponent fibers are disclosed in Davies U.S. Pat. No. 3,511,747 and Davies et al. U.S. Pat. No. 3,595,731.

Several thin absorbent panty liner products are now on the market which protect the wearer's undergarment both during intramenstrual use and in conjunction with other catamenial devices, during menstrual use. Such products are intended to provide the user with protection from the staining of undergarments, and particularly during non-menstruating days. These products generally are designed to be worn in the crotch portion of an undergarment and comprise a body facing side which is pervious to body fluids, an absorbent body which is capable of absorbing and retaining quantities of body fluid, and a fluid impermeable backing on the garment facing side of the product for preventing the fluid absorbed and retained from "striking through" onto the crotch surface of the undergarment. Generally, these products have been provided with a layer of pressure-sensitive adhesive adhering the product to the crotch portion of the garment. The layers of currently available panty liner products are primarily retained in assembled relationship with one another by the use of an additive adhesive.

It would be desirable to produce a laminated fabric structure without the use of an extraneous adhesive securing means, particularly in a product such as a panty liner.

BRIEF SUMMARY OF THE INVENTION

In accordance with the present invention there is provided a fibrous laminate, and method of making the same, giving improved resistance to delamination. In the laminate and method of the present invention, a first layer is secured to a second fibrous layer by thermobonding to fusible fibers entangled into at least the surface of the second layer adjacent the first layer. The first layer may comprise a film, but is preferably a fibrous layer. The fusible fibers retain their fibrous integrity after heat treatment to secure the layers, so that the preferred laminate is fibrous throughout. In a still preferred embodiment of the present invention the second fibrous layer is an entangled nonwoven fabric having fusible fibers disposed at least at the surface thereof adjacent the first layer. The second layer may however comprise a woven or nonwoven fibrous layer having fusible fibers entangled into said surface. The second layer may comprise base fibers and fusible fibers, and the opposite or second surface of the second layer may comprise predominantly base fibers, however, the present invention includes laminates wherein the second layer comprises a uniform distribution of fusible and base fibers. The present invention also includes the use of fusible fibers entangled into the second surface of the second layer for lamination to a third layer of film or fibers.

In accordance with a still preferred embodiment of the present invention, the fusible fibers incorporated into the second layer are conjugate fibers having several different polymer components present in side by side or sheath core relationship, at least 50 percent of the outer surface of such fibers comprises a low melting point component, having a temperature substantially less than the remaining high melting point component(s) thereof. By using such fibers, the high melting point component(s) will retain integrity as a fiber form after the low melting point component has been heat fused to the fibers of an adjacent fabric layer, thus continuing to contribute as a fiber to the nonwoven entangled fiber fabric. Specifically preferred is a sheath/core conjugate fiber. By using conjugate fibers wherein the core of the fiber is formed of the same material as the base fibers of the second fabric layer and concentrating such fibers at one major surface of the layer, after the sheath has been fused to the fibers of an adjacent fabric layer, the nonwoven entangled fiber fabric will be generally uniform in terms of physical properties.

When second fibrous layer as described above is incorporated into a product such as a panty liner, it is preferably associated with a body contacting fabric layer of the same size and shape, which sandwich therebetween an absorpent core and liquid repellent means. The second fibrous layer including fusible fibers concentrated at one face thereof is secured and laminated to the body contacting fibrous layer outwardly of the asorbent core and liquid repellent means and around the periphery thereof.

BRIEF DESCRIPTION OF THE DRAWINGS

The invention will be best understood by consideration of the following description taken together with the attached drawings in which.

DETAILED DESCRIPTION OF THE INVENTION

Figure 3:
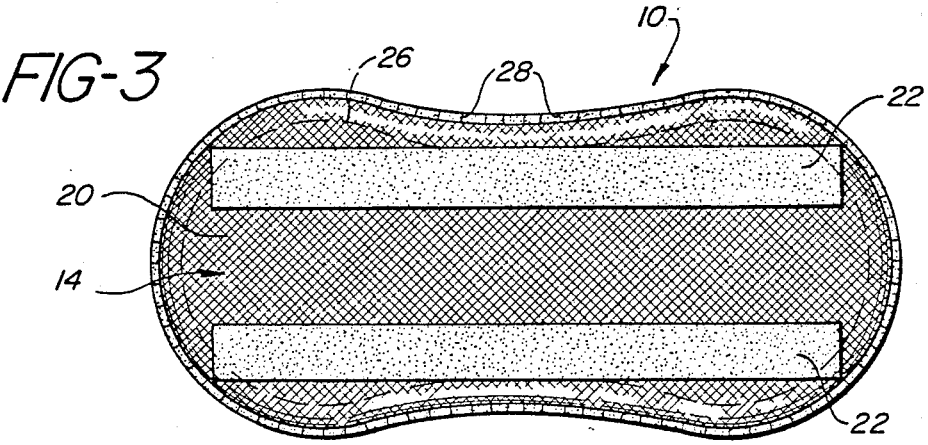
FIG. 3 is a plan view of the garment facing view of the panty liner of FIG. 1.
Figure 4:
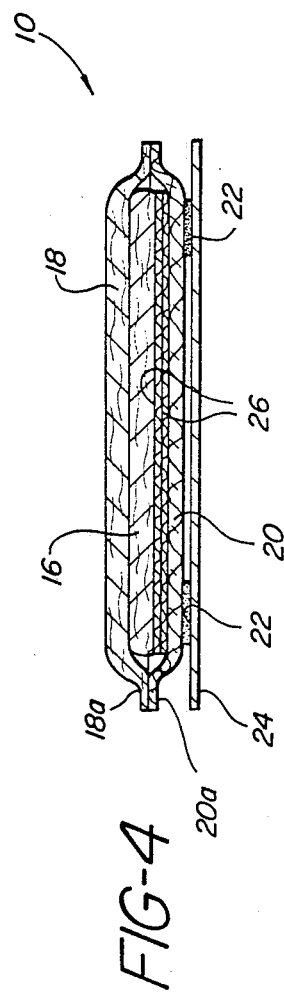
FIG. 4 is a transverse cross-sectional view of the panty liner of FIG. 2, taken through lines 4—4.
Figure 5:
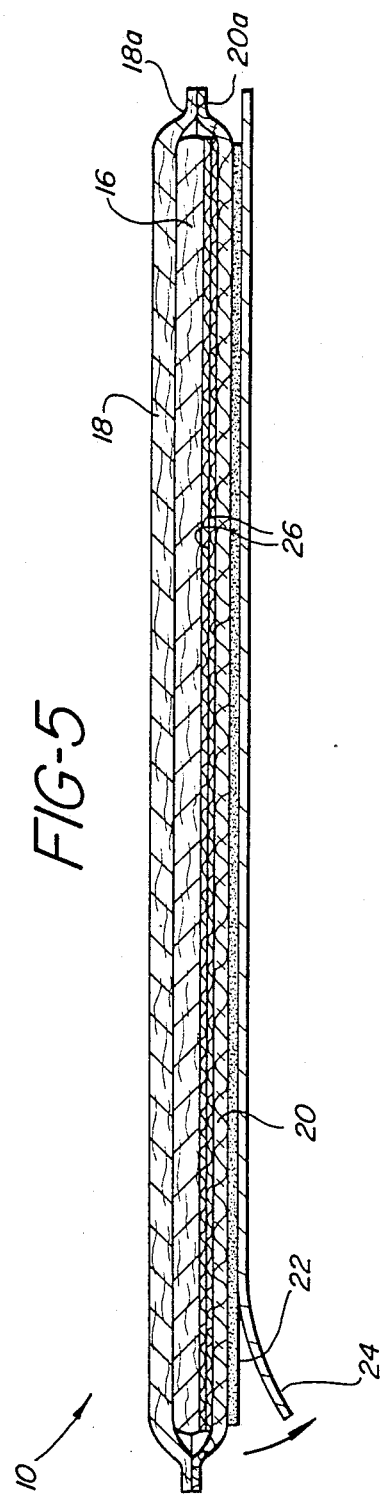
FIG. 5 is a longituinal, cross-sectional view of the panty liner of FIG. 2, taken through lines 5—5.

FIGS. 1-5 illustrate, in perspective, plan and cross-sectional views, a panty liner 10 incorporating the teachings of this invention. As best viewed in FIGS. 2 and 3, respectively, the panty liner comprises a body facing side 12 and a garment facing side 14. The body facing side of the liner consists of one or more plies of absorbent material 16 and may also include an outer cover 18 which may or may not be capable of absorbing and retaining body fluids, but, in any event, is pereable by such body fluids. The outermost surface of the body facing side of the liner 10 is provided with an aesthetically pleasing pattern of depressed areas which penetrate into the cover 18 and may also penentrate into one or more of the absorbent material plies 16. The garment facing side 14 includes a fibrous layer 20, comprising fusible fibers entangled into at least a surface thereof, hereafter described in detail, which cooperates with fibrous layer 18 to form the novel laminate of the present invention. Fibrous layer 20 is laminated at 18a and 20a to fibrous layer 18 outwardly of absorbent core 16 and liquid repellent means 26 around the perimeter of the panty liner as illustrated in FIGS. 4 and 5.

The choice of material for fibrous layer 18 of the liner may vary widely and may include, for example, woven or nonwoven fabrics or batts of absorbent materials such as comminuted wood pulp, rayon, cotton or other cellulosics including, for example, cellulosic materials which have been modified by chemcial treatment or otherwise to improve their absorbent characteristics. Other absorbent materials such as synthetic polymers in the form of fibers, or even flexible foams may be employed.

A particularly useful material is that recited in U.S. Pat. No. 3,663,238 issued on May 16, 1972 to G. J. Liloia et al. Described therein is a soft, lofty nonwoven comprising a mixture of approximately 25 percent, by weight, of relatively long (about 2.9 cm.) rayon fibers and about 75 percent, by weight, of short (about 0.2 cm.) wood pulp fibers and being stabilized by through bonding with a water dispersible binder present in an amount of between about 1 percent and about 30 percent of the weight of the fibers, on a dry basis. The binders of choice are the self-curing acrylic latex type, the urethane type or other similar binders.

Another particularly suitable absorbent material is a low density, highly absorbent, thermal bonded fabric comprising a mixture of absorbent fibers and staple length polyester/polyethylene conjugate fibers. The absorbent fibers are preferably wood pulp or other cellulosics which may have been treated to enhance absorbency. The conjugate fibers are fibers which comprise a polyester core surrounded by a sheath of polyethylene.

Preferably, the conjugate fibers employ high density polyethylene. That is, linear polyethylene that has a density of at least 0.94 and a Melt Index (as determined by ASTMD-1238E method, employing the parameters of 190° C. and 2160 gms) of greater than 1, preferably greater than about 10, and more preferably from about 20 to about 50. The fibers may comprise from about 40 to 60 percent, by weight polyester and, preferably, from 45 to 55 percent by weight polyester, with the remainder being polyethylene. Such fibers may be used in deniers of from 1 to about 6 and may be from about ½ inch (1.27 cm.) to about 3 to 4 inches (7.62 to 10.16 cms.) long. Preferably the fabric comprises outer layers of heat fusible fibers having the mixture of wood pulp and conjugate fibers sandwiched therebetween. Such outer layers may consist of the conjugate fibers or may in fact be any heat-fusible material such as polypropylene fibers, for example. The fabric is stabilized by applying heat thereto under essentially zero pressure whereby thermal bonding takes place without destroying the integrity of the fibers and a low density for the fabric is maintained. Typically, the bulk density of such fabrics is less than about 0.15 grams per cubic centimeter.

The outer cover 18 may also be of the typical fluid pervious materials used as covers for sanitary napkins such as a woven material e.g., gauze or, for example, a nonwoven material such as the ones described in U.S. Pat. No. 3,554,788 issued on Jan. 12, 1971, to M. R. Fechillas, which has the added advantage of being flushable i.e., may be disposed of by dispensing and flushing away in a water closet. The outer layer may also comprise the same material as that used as the one or more plies or absorbent material 16, provided of course, that such absorbent material has sufficient integrity in use to function as a cover for the panty liner of this invention. The aforementioned thermal bonded, conjugate fiber fabric is suitable for this purpose.

The second fibrous layer of the method and laminate of the present invention comprises a fibrous web of base fibers and fusible fibers. The fusible fibers are present at least along one major surface of the fibrous layer and may be present throughout the fibrous layer. It is preferred that the fusible fibers predominate. The fusible fibers at the said surface are entangled with the base fibers of the fibrous layer. With the use of entangled fusible fibers along the surface, a laminate having greater resistance to delamination than those formed using unentangled fusible fibers may be created. A number of different embodiments of the second fibrous layer are encompassed by the present invention.

Figure 6:
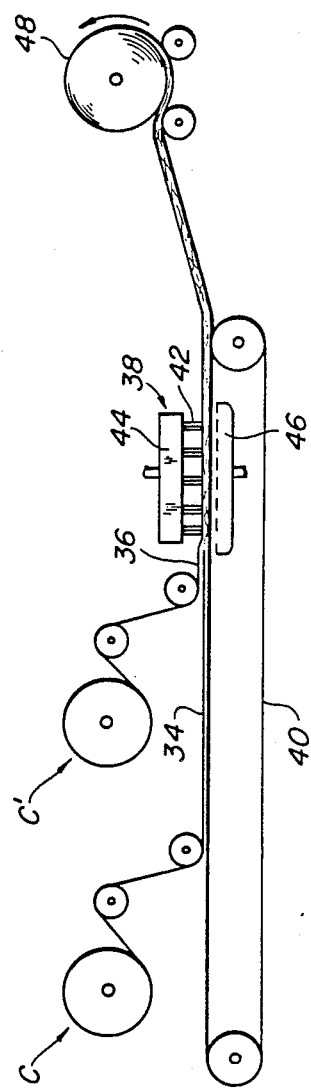
FIG. 6 is a schematic side elevation of an apparatus for producing an entangled fibrous layer which forms a part of the novel laminate, panty liner and method of the present invention.

FIG. 6 depicts a schematic representation of an apparatus for making a preferred embodiment of the second fibrous layer according to the method and laminate of the present invention. According to the schematic of FIG. 6, fusible fibers 36 are disposed atop a layer of base fibers 34 and directed through an entangling mechanism 38. As represented in FIG. 6, the fusible fibers and the base fibers may be provided by cards, C' and C. However, the present invention also contemplates the use of a nonwoven or woven fabric layer as the initial of base fibers, which nonwoven or woven fabric could be provided from an unwind station rather than a card. The fusible fibers entangled into the surface of the layer of base fibers forms the first surface of the second fibrous layer. If desired, fusible fibers may also be disposed against the opposite major surface of the layer of base fibers and entangled thereto to make subsequent lamination to yet another or third layer. Base fibers suitable for use in the present invention include synthetic or natural fibers, such as polyester, polypropylene, nylon, acrylic, rayon and cotton. The base fibers may also include fusible or conjugate fibers. In an alternative method of forming the second fibrous layer of the present invention, the base fibers and fusible fibers may be combined in a dual rotor mechanism of the type disclosed in Ruffo et al U.S. Pat. No. 3,768,118. The disclosure of which is hereby incorporated. The dual rotor mechanism can be readily adjusted to provide a web containing a mixture of fusible and base fibers and specifically to provide a preferred embodiment of a web wherein one major surface is comprised predominantly of fusible fibers and the other major surface is comprised predominantly of base fibers. The web provided by the dual rotor may then be directed through an entangling mechanism such as shown at 38. Fusible fibers suitable for use in the present invention include conjugate fibers or homofil fusible fibers, such as low melt polyester or polypropylene. However, it is preferred to use conjugate fibers as the fusible fibers because of the ease with which such fibers may be thermobonded while maintaining their fibrous integrity, or low bulk density characteristics of the web. The conjugate fibers have a low melting point component and a high melting point component. In the thermobonding process, the low melting point component is used to thermobond to other fibers, e.g., a film, and the low melting point component retains its fibrous integrity. It is also possible to use homofil fusible fibers in the method and laminate of the present invention. However, care must be taken in choosing the processing conditions to achieve thermobonding of the homofil fusible fibers to other fibers or to a film while still maintaining the fibrous integrity of the homofil fiber.

An example of conjugate fibers useful in the present invention are polyester/polyethylene conjugate fibers wherein at least about 50 percent of the surface of the individual conjugate fibers is polyethylene. It is preferred to use sheath/core fibers with polyethylene as the sheath and polyester as the core. Preferably, the conjugate fibers are the polyethylene/polyester conjugate fibers described above in relation to the first fibrous layer.

Figure 7:
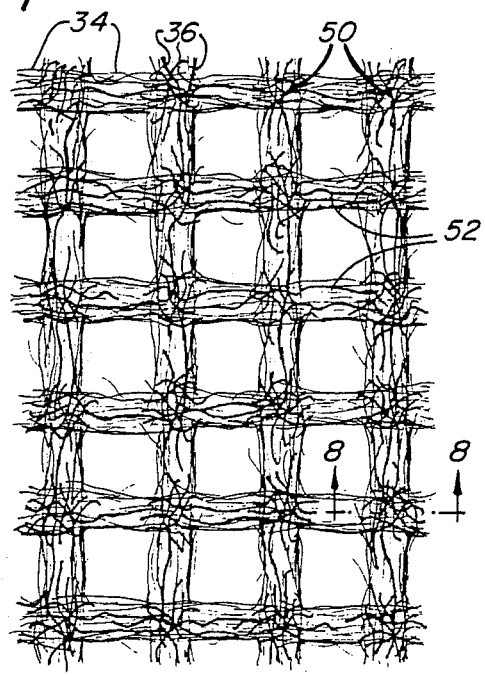
FIG. 7 is an enlarged plan view of the composite fabric produced by the apparatus of FIG. 6.
Figure 8:
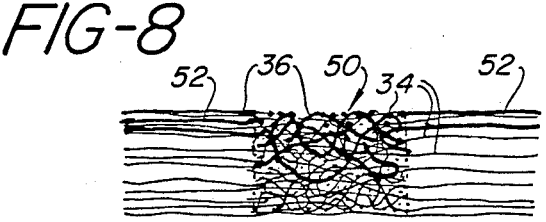
FIG. 8 is a view taken along line 8—8 of FIG. 7.

As shown in FIG. 6, the base fibers and fusible fibers are disposed on an endless belt 40 and conveyed into an entangling mechanism 38 of the type shown in Evans U.S. Pat. No. 3,485,706 where a series of high pressure, fine, essentially columnar jets of water 42 impact the web, entangling the fibers. The high pressure water is supplied form a manifold 44. The jets are arranged in rows disposed transversely across the path of travel of the belt 40, preferably there is a vacuum means 46 pulling a vacuum, e.g, of up to 5 to 10 inches of mercury, beneath the belt 40 with a vacuum slot positioned directly under each row of jets 42. If the layer of base fibers 34 is a nonwoven or woven fabric layer, sufficient water pressure and/or number of jets to entangle the fusible fibers into the base fibers must be used. If the layer of base fibers 34 is a loose array of carded or air-laid base fibers, the base fibers and fusible fibers may be entangled into a number of fabric configurations as is well known in the art. For instance, the base and fusible fibers of the second fibrous layer may be entangled into a regular repeating pattern of lightly entangled fiber regions of higher density than the average density of the layer and interconnecting fibers extending between the lightly entangled fiber regions, said interconnecting fibers being randomly entangled with each other in said lightly entangled regions. In a preferred embodiment, the base and fusible fibers of the second fibrous layer may be formed into an apertured entangled fibrous layer. The fibers may be entangled and rearranged into a regular repeating pattern of entangled fiber regions and interconnecting fibers extending between the entangled regions and entangled therein, wherein the interconnecting fibers are disposed in a multiple intersecting series of bands, wherein in each series the bands are substantially parallel to each other, and each band contains segments in which the individual interconnecting fibers are substantially parallel to each other, which segments alternate with entangled fiber regions, and said segments and entangled fiber regions define a regular repeating pattern of apertures through the layer. The method of forming such an entangled structure is set out in U.S. patent application Ser. No. 341,924. Such an apertured entangled second fibrous layer is depicted in FIG. 7 and FIG. 8. In the preferred embodiment shown in FIGS. 7 and 8, fusible fibers are concentrated at one surface of the fabric. The fusible fibers are entangled with the base fibers and the base fibers are entangled with each other and with the fusible fibers. As shown in FIG. 7, both base fibers 34 and fusible fibers 36 are present in the entangled regions 50, and are disposed substantially parallel to each other in the segments 52 of interconnecting fibers. In FIG. 7, one series of bands is disposed horizontally and the other vertically. The segments 52 in the entangled regions 50 define a regular repeating pattern of apertures through the fabric.

As shown in FIG. 8, depicting a cross-section taken along line 8—8 of FIG. 7, fusible fibers 36 and base fibers 34 are present in both the entangled regions 50 and the segments 52 of interconnecting fibers. The fusible fibers, present at a surface of the fibrous layer, are entangled with base fibers in the entangled regions 50. While it is preferred to provide one surface of the layer enriched with fusible fibers, it should be understood that the layer could be formed entirely of fusible fibers. In a most preferred embodiment of the second fibrous layer of the present invention, the layer comprises 80 percent polyester and 20 percent polyethylene/polyester conjugate fibers. However, laminate products according to the present invention may be made utilizing a second fibrous layer comprising 10 percent conjugate fibers, or more specifically, a second fibrous layer wherein the first surface comprises 10 percent conjugate fibers.

Figure 1:
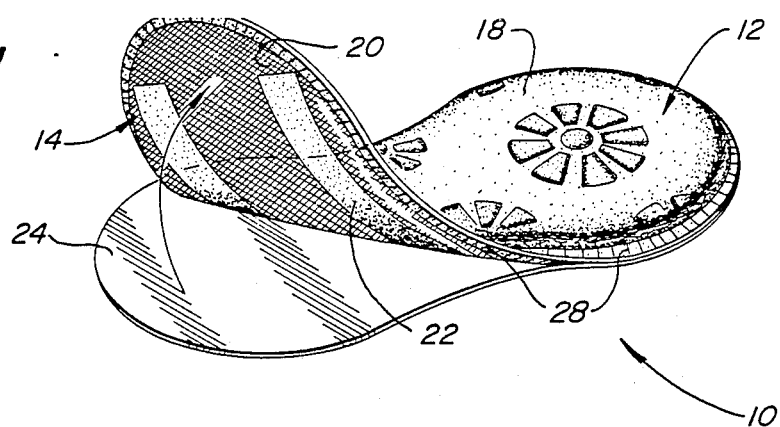
FIG. 1 is a perspective view of the panty liner of this invention with the adhesive protecting release layer being partially removed for clarity.
Figure 2:
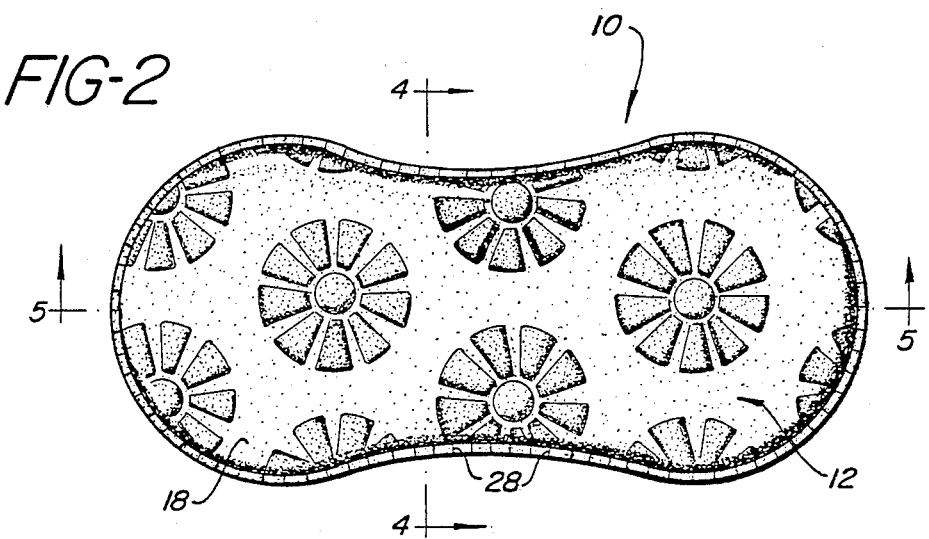
FIG. 2 is a plan view of the body facing side of the panty liner of FIG. 1.

Referring to the panty liner depicted in FIGS. 1–5, overlying one or more areas on the outer surface of the backing 20 which may be, e.g., a second fibrous layer as shown in FIGS. 7 and 8, adhesive layers 22 comprising pressure-sensitive adhesive for adhering the panty liner to the crotch portion of the wearer's undergarment. As best illustrated in FIG. 3, such areas comprise two longitudinally extending bands of pressure-sensitive adhesive. Although it will be understood by those skilled in the art that many variations and the number and shape of these adhesive areas are possible. As illustrated in FIGS. 1, 4 and 5, the adhesive areas 22 are protected by a release strip 24 to avoid undesired adhesion prior to use. The release strip 24 may be made of any suitable sheet-like material which adheres with sufficient tenacity to the adhesive area 22 to remain in place but which can also be readily removed when the panty liner is to be used.

The present invention contemplates that a wide variety of different means may be utilized to thermally bond the first and second layers to form the novel laminate of the present invention. Such means include heated calender rolls, heated platens, and hot air ovens, etc., so long as sufficient heat is generated at the interface between the layers to thermobond the fusible fibers at the first surface of the second layer to the first layer.

A technique that is particularly well suited for the purpose of the present invention and in particular to unite the layers 18 and 20 of the panty shield of the present invention is the application of ultrasonic energy, since such techniques tend to concentrate the applied energy to the interface between the layers to be joined. An apparatus suitable for this purpose is commercially available from Branson Instruments, Inc. of Stanford, Connecticut, and includes an anvil and horn between which the layers to be joined are compressively engaged, with the horn transmitting vibrations in the ultrasonic frequency to the layers to be joined, when the horn is energized.

The foregoing description and drawings are illustrative but are not to be taken as limiting. Other variations and modifications are possible without departing from the spirit and scope of the present invention.

I claim:

1. A panty liner to be worn in the crotch portion of an undergarment comprising: a first fibrous layer having first and second oppositely facing major surfaces, said first major surface of said first fibrous layer being adapted to be disposed against the body; an absorbent core smaller in external dimensions than said first fibrous layer and positioned in juxtaposed relationship with respect to the second major surface thereof; liquid repellent means generally coextensive in external dimension with the external dimensions of said absorbent core and positioned in juxtaposed relationship with respect thereto; and a second fibrous layer of base fibers and fusible fibers, said layer having substantially the same size and shape as said first fibrous layer, said second fibrous layer having first and second oppositely facing major surfaces, the first major surface of said second fibrous layer being positioned in face-to-face juxtaposition with said liquid repellent means and with the peripheral portion of the second major surface of said first fibrous layer outwardly of said liquid repellent means, the fibers in said second fibrous layer being arranged in a regular repeating pattern of entangled region of higher density than the average density of the layer and interconnected fibers extending between the entangled fiber regions, said interconnecting fibers being randomly entangled with each other in said entangled regions, said heat fusible fibers being present at least at the first major surface of said second fibrous layer, at least some of said heat fusible fibers in the peripheral portion of said second fibrous layer being fused to fibers in the peripheral portion of said first fibrous layer, whereby said first and second fibrous layers are secured to one another and said absorbent core and said liquid repellent means are retained therebetween.

2. A panty liner as in claim 1 wherein said interconnecting fibers of said second fibrous layer are disposed in multiple intersecting series of bands wherein, in each series the bands are substantially parallel to each other, and each band contain segments in which the individual interconnecting fibers are substantially parallel to each other, which segments alternate with said entangled fiber regions, and said segments and entangled fiber regions define a regular repeating pattern of apertures through said layer.

3. A panty liner as set forth in claim 1 wherein the peripheral portions of said first and second fibrous layers are secured to one another at spaced securement zones disposed around the periphery thereof.

4. A panty liner as set forth in claim 1 wherein the first major surface of said second fibrous layer includes a higher percentage of said heat fusible fibers than the second major surface of said second fibrous layer and the second major surface of said second fibrous layer includes a higher percentage of said base fibers than the first major surface of said second fibrous layer.

5. A panty liner as set forth in claim 4 wherein said second fibrous layer contains at least about 10 percent heat fusible fibers.

6. A panty liner as set forth in claim 5 wherein said second fibrous layer contains from about 10 to about 90 percent heat fusible fibers.

7. A panty liner as set forth in claim 6 wherein said heat fusible fibers are conjugate fibers which comprise a low melting point component and a high melting point component, and wherein the low melting point component occupies at least 50 percent of the surface of the conjugate fibers.

8. A panty liner as set forth in claim 7 wherein the high melting point component of said conjugate fibers and said base fibers are formed of the same material.

9. A panty liner as set forth in claim 8 in which said base fibers and the high melting point component of said conjugate fibers are polyester, and wherein the low melting point component of said conjugate fibers is polyethylene.

10. A panty liner as set forth in claim 9 in which the polyethylene and polyester components of said conjugate fibers are present in a sheath/core configuration, in which the polyester forms the core, and the polyethylene forms the sheath of the fibers.

11. A panty liner as set forth in claim 10 wherein pressure sensitive adhesive means is provided on the second major surface of said second fibrous layer for adherence to a garment such as a panty.

* * * * *